United States Patent
Ma et al.

(10) Patent No.: US 9,493,399 B2
(45) Date of Patent: *Nov. 15, 2016

(54) MULTI-BRANCHED MANNICH BASE CORROSION INHIBITOR AND PREPARATION METHOD THEREOF

(75) Inventors: Ling Ma, Beijing (CN); Lei Li, Beijing (CN); Xiangjun Kong, Beijing (CN); Malike Dilibai, Beijing (CN); Xinping Zhen, Beijing (CN); Chunge Niu, Beijing (CN); Shengjun Bai, Beijing (CN)

(73) Assignee: PETROCHINA COMPANY LIMITED, Beijing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 14/234,854

(22) PCT Filed: Apr. 27, 2012

(86) PCT No.: PCT/CN2012/000567
§ 371 (c)(1),
(2), (4) Date: Apr. 29, 2014

(87) PCT Pub. No.: WO2013/026252
PCT Pub. Date: Feb. 28, 2013

(65) Prior Publication Data
US 2014/0296575 A1    Oct. 2, 2014

(30) Foreign Application Priority Data

Aug. 19, 2011 (CN) .......... 2011 1 0238857

(51) Int. Cl.
| | | |
|---|---|---|
| *C07C 225/06* | (2006.01) | |
| *C10G 75/02* | (2006.01) | |
| *C23F 11/14* | (2006.01) | |
| *C07C 221/00* | (2006.01) | |
| *C07C 225/10* | (2006.01) | |
| *C07C 225/12* | (2006.01) | |
| *C07C 225/16* | (2006.01) | |

(52) U.S. Cl.
CPC ........... *C07C 225/06* (2013.01); *C07C 221/00* (2013.01); *C07C 225/10* (2013.01); *C07C 225/12* (2013.01); *C07C 225/16* (2013.01); *C10G 75/02* (2013.01); *C23F 11/141* (2013.01)

(58) Field of Classification Search
CPC ...................................................... C07C 225/06
See application file for complete search history.

(56) References Cited

FOREIGN PATENT DOCUMENTS

| CN | 1419573 A | 5/2003 |
|---|---|---|
| CN | 1761715 A | 4/2006 |
| CN | 101158043 A | 4/2008 |
| CN | 101182296 A | 5/2008 |
| CN | 101451242 A | 6/2009 |
| CN | 100577877 C | 1/2010 |
| RU | 4-1550919 A1 | 10/1992 |

OTHER PUBLICATIONS

PCT International Search Report dated Sep. 8, 2012 for PCT/CN/2012/000567, from which the instant application is based, 2 pgs.

*Primary Examiner* — Clinton Brooks
(74) *Attorney, Agent, or Firm* — Fredrikson & Byron, P.A.

(57) ABSTRACT

The present invention relates to a multi-branched Mannich base corrosion inhibitor and the method for preparing thereof. The method comprises (1) adding 3~7 moles ketone and 3~7 moles aldehyde to reaction kettle, adjusting pH to 2~6 with acid, controlling temperature to 20~50° C. and stirring for 20~30 mins; (2) adding 1 mole organic polyamine to the reaction kettle under stirring, or adding the pH-adjusted ketone, aldehyde and organic solvent to organic polyamine, controlling temperature to 60~90° C. and reacting for 1~3 hrs, and after completion of the reaction, heating the system to 110° C. under nitrogen to remove water; the organic polyamine is organic compound comprising three or more primary amine groups and/or secondary amine groups. The Mannich base corrosion inhibitor of the present invention shows characters of strong adsorption force, high film strength, high film compactness, increase in corrosion inhibition efficiency by at least 2%, and overcomes the disadvantages in prior art of few adsorption centers, single adsorption group and weak adsorption force to metal surfaces.

8 Claims, No Drawings

MULTI-BRANCHED MANNICH BASE CORROSION INHIBITOR AND PREPARATION METHOD THEREOF

RELATED APPLICATIONS

This application is a 35 U.S.C. 371 national stage filing from International Application No. PCT/CN2012/000567 filed Apr. 27, 2012 and claims priority to Chinese Application No. 201110238857.3 filed Aug. 19, 2011, the teachings of which are incorporated herein by reference.

FIELD OF THE INVENTION

The present invention relates to a multi-branched Mannich base corrosion inhibitor and the preparation method thereof.

BACKGROUND OF THE INVENTION

Mannich Reaction, also referred to as amine methylation reaction, is an important organic reaction developed progressively since early 20$^{th}$ century and was named after Germany chemist Carl Ulvich Franz Mannich (1877-1947). Mannich found in 1917 that the reaction of amine hydrochlorides, formaldehyde and C—H acid compounds, in particular ketones, can produce ketone bases. Moreover, substances of characters similar to alkaloids can be produced by appropriate selection of reaction components. Thereafter, a number of research reports were delivered by Mannich school. Specifically, reactions with aliphatic ketones, aromatic ketones and alicyclic ketones as the acid component were intensively investigated, thereby establishing the basis of Mannich reaction. Mannich bases and derivatives thereof were firstly used as medicaments. As time goes on, the products of Mannich reaction are widely spread in various fields of consumer goods production, for example, they can be used for the synthesis of sedative, acesodyne, fungicide, oedema inhibitor, antineoplastic, hepatic protectant, anticoagulant and the like in terms of medicament, and they also found use in terms of explosive, propellant, polymeric flocculant, corrosion inhibitor, vulcanizing accelerator, phytocide, dispersant, antioxidant, active dye, food flavorant, metal chelator.

The application of Mannich bases as corrosion inhibitor started from 1970's. Mannich bases were initially used as preservative in antifreezing solution, and consequently used for treating the inner walls of the reservoir of petroleum gas. As the increase of the well depth in oil exploration and exploitation, and the wide use of technique for increasing the production of crude oil by oil well acidification, the need for high temperature acidizing corrosion inhibitor causes the popularizing of the application of Mannich base type corrosion inhibitor.

Documents and patents related to Mannich base type corrosion inhibitor are mainly:

Xiaoyun Duan and Pengjiang Li synthesized Mannich base type corrosion inhibitors by means of Mannich reaction using formaldehyde, cyclohexylamine and acetophenone as the primary raw materials, and investigated the effect of the ratio of formaldehyde, cyclohexylamine and acetophenone on the corrosion inhibition property of the synthesized Mannich base type corrosion inhibitor (Xiaoyun Duan and Pengjiang Li, Synthesis of a Mannich Base Inhibitor, Technology & Development of Chemical Industry, 2008, 37(9), 11-12); document "Synthesis and Performance Evaluation of YZ-1 Acidizing Corrosion Inhibitor" reported a Mannich base acidification corrosion inhibitor YZ-1 synthesized via Mannich reaction with formaldehyde, acetone and ethylenediamine as the raw materials. The corrosion inhibitor YZ-1 exhibits good inhibition in hydrochloric acid, hydrofluoric acid and mud acid, and tolerates a temperature up to 150° C. (Haihong Zheng, Jianbo Li, Zhibing Mo et al., Synthesis and Performance Evaluation of YZ-1 Acidizing Corrosion Inhibitor, Corrosion & Protection in Petrochemical Industry, 2008, 25(4), 8-10); Faguo Tian, Jianbo Li, Zilin Yan et al. of Southwest Petroleum University prepared Mannich base via Mannich reaction with formaldehyde, acetophenone and ethylenediamine as the raw materials, followed by quaternization with benzyl chloride to obtain Mannich base quaternary ammonium salt. The resulting corrosion inhibitor exhibits good solubility in acid and good compatibility with other acidizing additives, and is non-toxic and resistant to high temperature, and exhibits good corrosion inhibition in different acid solutions (Faguo Tian, Jianbo Li, Zilin Yan et al., Preparation and Performance Evaluation of a novel high temperature acidizing corrosion inhibitor SYB for oil well, Chemical Engineering of Oil & Gas, 2009, 38(5), 426-429); paper "Study and Development of a Mannich Based Corrosion Inhibitor for Hydrochloric Acid acidifying" reports a low cost Mannich base developed using cyclohexylamine. The Mannich base can be used as the primary inhibitor of acidizing corrosion inhibitor for oil gas well. The corrosion test indicates that only 0.5% of the Mannich base is required to be added into 20% industrial hydrochloric acid at 60° C. to satisfy the requirement of first grade acidizing corrosion inhibitor in the industrial standard for petroleum and gas (Jingguang Wang, Hongjiang Yu, Qianding Li, Study and Development of a Mannich Based Corrosion Inhibitor for Hydrochloric Acid acidifying, Journal of Xi'an Shiyou University (Natural Science Edition), 2007, 22(3), 77-79); Chinese patent CN 100577877C discloses a method for synthesizing Mannich base steel corrosion inhibitor mother liquor and steel corrosion inhibitor mother liquor. Steel corrosion inhibitor is prepared by Mannich reaction of secondary amine, aldehyde and alkyl, cycloalkyl, aryl or haloalkyl, cycloalkyl and aryl ketone in aqueous medium; CN101451242A "High temperature acidified corrosion inhibitor for oil passageway containing Cr" discloses an acidified corrosion inhibitor, whose main agent A comprises the following compositions: 25 to 35 parts of quinoline quaternary ammonium salt or quinoline derivate quaternary ammonium salt, 5 to 10 parts of potassium iodide, and 40 to 60 parts of organic solvent methanol or formaldehyde, and an addition agent B comprises the following compositions: 30 to 50 parts of Mannich base, 15 to 35 parts of propiolic alcohol, 5 to 15 parts of chromic chloride, and 20 to 35 parts of formaldehyde. During use, the proportion of A to B is 2-1.5:1; CN 1761715A synthesizes Mannich base curing agents of epoxide or polyurethane system from phenolic compound, formaldehyde and at least one polyamine. An excess of amine is used, so that the phenolic compounds react as completely as possible and are not left to make the product less environmental friendly. CN101182296A also reports a curing agent for epoxy or polyurethane system, prepared from cyclohexanone dimer, formaldehyde and at least one polyamine, with the amine used in excess.

The raw materials for synthesizing Mannich corrosion inhibitors in prior art are primarily (1) ketone, mainly aliphatic ketone such as acetone, butanone, pentanone, hexanone and the like), cycloalkanone such as cyclohexanone, and aromatic ketone such as acetophenone; (2) aldehyde, generally formaldehyde or polyformaldehyde; (3) amine, mainly aliphatic amine such as diethanol amine, dimethylamine, diethylamine, ethylenediamine, aliphatic polyamine, naphthenic amine such as cyclohexylamine, morpholine and the like, aromatic amine such as aniline, benzylamine, aromatic polyamine and the like. The ratio of ketone, aldehyde and amine (monamine) in prior art is 1:1:1 or the ratio of ketone, aldehyde and amine (diamine) is 2:2:1, and thus the resulting Mannich base has a linear structure:

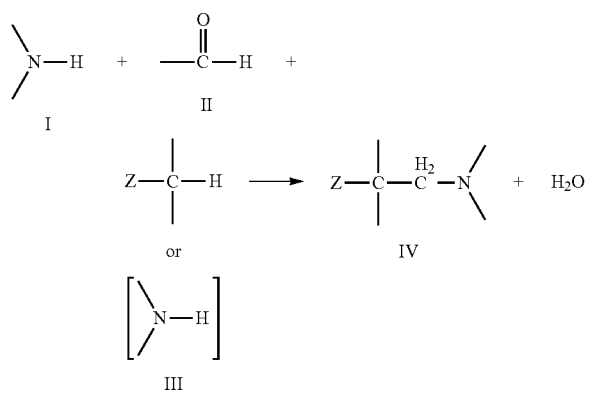

I: primary, secondary amine or ammonia
II: formaldehyde or other aldehydes
III: compound comprising one or more active hydrogen
IV: Mannich base
Z: electron-withdrawing group The adsorption center of the linear Mannich corrosion inhibitor is located at one end or both ends of the molecule. When the linear Mannich corrosion inhibitor encounters metal wall surfaces, it exhibits terminal group adsorption with one end containing adsorption center forming chemical or physical adsorption with the metal while the other end extending outwards to form hydrophobic layer. The disadvantage of the linear Mannich corrosion inhibitor forming film on the metal surface lies in the low cohesion, low film strength, bad film compactness and bad corrosion inhibiting capability due to single-point adsorption between the corrosion inhibitor and the metal wall surface. In particular, the linear Mannich corrosion inhibitor is difficult to form or cannot form film on corroded or unsmooth metal wall surfaces.

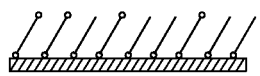

The adsorption of linear Mannich corrosion inhibitor on metal surface

SUMMARY OF THE INVENTION

The object of the present invention is to provide a Mannich base having multi-branched stereo structure, also referred to as chiral Mannich base corrosion inhibitor, which is prepared from ketone, aldehyde and organic polyamine containing three or more primary amine groups and/or secondary amine groups via Mannich reaction, the molar ratio of the starting materials is ketone: aldehyde: organic polyamine=$X_1$: $X_2$: 1, wherein $X_1 > 2$ and $X_2 > 2$. The following multi-branched structure of Mannich base corrosion inhibitor is obtained by causing at least two primary amine groups or secondary amine groups on the organic polyamine to undergo Mannich reaction with ketone and aldehyde respectively, that is, the organic polyamine is sufficiently utilized to perform the grafting of the functional groups on a plurality of amine groups.

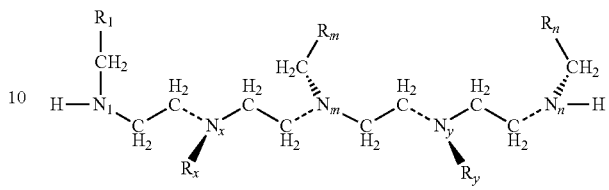

wherein
$N_1$, $N_x$, $N_y$, $N_m$, and $N_n$ are nitrogen atoms on C—N skeleton, x, y, m and n are sequence number thereof, $2 \leq x \leq m \leq y \leq n-1$, and $3 \leq n \leq 7$;

$R_1$, $R_m$ and $R_n$ are substituents in starting material ketone after the substitution of active hydrogen on the carbon atom linked to carbonyl, and may be aliphatic ketone group, alicyclic ketone group and aromatic ketone group, respectively. The ketone group within the ring of alicyclic ketone group includes cyclohexanone group, cyclopentanone group, o-methyl cyclohexanone group, p-methyl cyclohexanone group, 2-methyl cyclopentanone group, 2-ethyl cyclopentanone group, 3-ethyl cyclopentanone group. Aliphatic ketone group, aromatic ketone group and other alicyclic ketone group can be represented by the following formula:

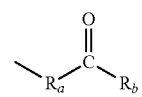

$R_x$ and $R_y$ may be H or

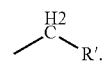

R' is substituent in starting material ketone after the substitution of active hydrogen on the carbon atom linked to carbonyl, and may be aliphatic ketone group, alicyclic ketone group and aromatic ketone group, respectively. The ketone group within the ring of alicyclic ketone group includes cyclohexanone group, cyclopentanone group, o-methyl cyclohexanone group, p-methyl cyclohexanone group, 2-methyl cyclopentanone group, 2-ethyl cyclopentanone group, 3-ethyl cyclopentanone group. Aliphatic ketone group, aromatic ketone group and other alicyclic ketone group can be represented by the following formula:

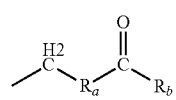

$R_a$ and $R_b$ each independently represents $C_1 \sim C_6$ alkyl, $C_6 \sim C_9$ linear or branched aryl, $C_5 \sim C_9$ linear or branched cycloalkyl group.

Another object of the present invention is to provide a method for preparing Mannich base corrosion inhibitor, which is prepared from Mannich reaction using ketone that can be aliphatic ketone, alicyclic ketone or aromatic ketone, formaldehyde or compound capable of dissociating out formaldehyde, and organic polyamine containing three or more primary amine group and/or secondary amine group as the starting materials. The method has a simple preparation process, mild reaction condition, readily available starting materials, and low energy consumption.

One of the technical solutions provided by the present invention is to provide a Mannich corrosion inhibitor prepared from 1 mole organic polyamine with 3~7 moles ketone and 3~7 moles aldehyde via Mannich reaction.

The organic polyamine is organic compounds containing three or more primary amine group and/or secondary amine group, and is selected from the group consisting of diethylenetriamine, triethylenetetramine, tetraethylenepentamine, pentaethylenehexamine, hexaethyleneheptamine or combinations thereof.

The ketone is selected from the group consisting of aliphatic ketone, alicyclic ketone, aromatic ketone or combinations thereof. The ketone group within the ring of alicyclic ketone group includes cyclohexanone group, cyclopentanone group, cycloheptanone group, o-methyl cyclohexanone group, p-methyl cyclohexanone group, 2-methyl cyclopentanone group, 2-ethyl cyclopentanone group, 3-ethyl cyclopentanone group. Aliphatic ketone group, aromatic ketone group and other alicyclic ketone group can be represented by the following formula:

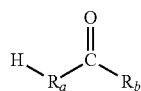

wherein $R_a$ and $R_b$ each independently represents $C_1$~$C_6$ alkyl, $C_6$~$C_9$ linear or branched aryl, $C_5$~$C_9$ linear or branched cycloalkyl group.

The aldehyde is formaldehyde or polyformaldehyde, a compound capable of dissociating out formaldehyde, preferably formaldehyde.

Another technical solution provided by the present invention is to provide a method for preparing Mannich base corrosion inhibitor, which consists in adding excess amount of ketone and aldehyde, and causing at least three primary amine group and/or secondary amine group on organic polyamine to undergo Mannich reaction with said ketone and aldehyde to form multi-branched Mannich base corrosion inhibitor. Specifically, the method comprises (1) adding 3~7 moles ketone and 3~7 moles aldehyde to reaction kettle, adjusting pH to 2~6 with acid, controlling temperature to 20~50° C. and stirring for 20~30 mins; (2) adding 1 mole organic polyamine to the reaction kettle under stirring, or adding the pH-adjusted ketone, aldehyde and organic solvent to organic polyamine, controlling temperature to 60~90° C. and reacting for 1~3 hrs, and after completion of the reaction, heating the system to 110° C. under nitrogen to remove water.

A more preferred method comprises (1) adding 3~7 moles ketone and 3~7 moles aldehyde to reaction kettle, adjusting pH to 2~4 with acid, controlling temperature to 30~40° C. and stirring for 20~30 mins; (2) adding 1 mole organic polyamine and organic solvent to the reaction kettle under stirring, controlling temperature to 70~85° C. and reacting for 1.52.5 hrs, and after completion of the reaction, heating the system to 110° C. under nitrogen to remove water.

The organic solvent added during the reaction is one of methanol, ethanol and petroleum ether, preferably ethanol. The acid used for adjusting pH value is one of hydrochloric acid, formic acid and acetic acid, preferably hydrochloric acid.

The way to add the starting materials in the method described above is to add organic polyamine to ketone and aldehyde, or to add ketone and aldehyde to organic polyamine, and the preferred way is to add organic polyamine to ketone and aldehyde.

DETAILED DESCRIPTION OF THE INVENTION

Examples of the preparation of Mannich base corrosion inhibitor and evaluation of corrosion:

| Mannich base | Example 1 | Example 2 | Example 3 | Example 4 | Example 5 | Example 6 | Example 7 | Example 8 | Example 9 | Example 10 | Example 11 | Example 12 |
|---|---|---|---|---|---|---|---|---|---|---|---|---|
| Organic polyamine (mol) | | | | | | | | | | | | |
| Diethylenetriamine | 1 | | | | | | | | | | | |
| Pentaethylenehexamine | | 1 | | | | | | | | 0.5 | | |
| Tetraethylenepentamine | | | 1 | | | | | | | | | 0.2 |
| Triethylenetetramine | | | | 1 | | | | | | | 0.2 | |
| Hexaethyleneheptamine | | | | | 1 | | | | | 0.5 | | |
| Triethylenetetramine | | | | | | 1 | | | | | | |
| Tetraethylenepentamine | | | | | | | 1 | | | | | |
| Diethylenetriamine | | | | | | | | 1 | | | 0.8 | 0.2 |
| Triethylenetetramine | | | | | | | | | 1 | | | 0.6 |
| Ketone (mol) | | | | | | | | | | | | |
| Cyclohexanone | 3 | | 5 | | | 1 | | | | | | |
| 2-methylcyclopentanone | | | | | 7 | | | 3 | | 1 | | |
| Pentanone | | | | | | 2 | 0.5 | | | | 3.5 | |
| Acetophenone | | 6 | | 4 | | | 0.5 | | 4 | 1 | | |
| Acetone | | | | | | 2 | | | | | | 4.5 |
| Butanone-2 | | | | | | | 2 | | | 3.5 | | |
| Aldehyde (mol) | | | | | | | | | | | | |
| Formaldehyde | 3 | 6 | 2 | 4 | 7 | 5 | 6 | | 4.5 | 5.5 | 3.5 | 6 |
| Trioxane (equivalent formaldehyde) | | | 3 | | | | | 3 | | | | |

-continued

| Mannich base | Example 1 | Example 2 | Example 3 | Example 4 | Example 5 | Example 6 | Example 7 | Example 8 | Example 9 | Example 10 | Example 11 | Example 12 |
|---|---|---|---|---|---|---|---|---|---|---|---|---|
| Preparation condition | | | | | | | | | | | | |
| pH value | 2 | 2 | 3 | 5 | 5 | 4 | 3 | 3 | 3 | 3 | 2 | 2 |
| Reaction temperature of polyamine (° C.) | 80 | 85 | 80 | 75 | 78 | 65 | 70 | 90 | 85 | 60 | 80 | 80 |
| Reaction time of polyamine (h) | 1.5 | 2 | 2 | 2 | 2.5 | 3 | 2.5 | 1 | 2.5 | 3 | 2 | 2 |
| Results of corrosion evaluation | | | | | | | | | | | | |
| Corrosion rate (g/m$^2$ · h) | 3.81 | 4.88 | 4.56 | 1.98 | 1.86 | 2.35 | 9.65 | 4.54 | 7.35 | 5.47 | 11.27 | 2.18 |
| Corrosion inhibition efficiency (%) | 96.83 | 95.93 | 96.20 | 98.35 | 98.45 | 98.04 | 91.96 | 96.22 | 93.88 | 95.44 | 90.61 | 98.18 |
| Corrosion inhibitor rating | Grade 1 | Grade 2 | Grade 2 | Grade 1 | Grade 1 | Grade 1 | Grade 3 | Grade 2 | Grade 3 | Grade 3 | — | Grade 1 |

COMPARISON EXAMPLE 1

Preparation conditions: pH=2, reaction temperature=80° C., reaction time=1.5 h, that is, the reaction condition of example 1.

Molar ratio of the starting materials: diethylenetriamine: cyclohexanone: formaldehyde=1:2:2

Results of corrosion evaluation: corrosion rate=6.21 g/m$^2$·h, corrosion inhibition efficiency=94.83%, corrosion inhibitor rating: Grade 3

Molar ratio of the starting materials: diethylenetriamine: cyclohexanone: formaldehyde=1:1:1

Results of corrosion evaluation: corrosion rate=14.13 g/m$^2$·h, corrosion inhibition efficiency=88.23%, corrosion inhibitor rating:

Conclusion: Compared with the corrosion inhibitor prepared with molar ratio of diethylenetriamine: cyclohexanone: formaldehyde=1:2:2 and 1:1:1, when the molar ratio of the starting materials is the feeding ratio of example 1, that is, diethylenetriamine: cyclohexanone: formaldehyde=1:3:3, the corrosion inhibition efficiency increases by 2% and 8.6% respectively, and the corrosion inhibitor rating increases two and at least three grades, respectively.

COMPARISON EXAMPLE 2

Preparation conditions: pH=2, reaction temperature=85° C., reaction time=2 h, that is, the reaction condition of example 2.

Molar ratio of the starting materials: pentaethylenehexamine: acetophenone: formaldehyde=1:2:2

Results of corrosion evaluation: corrosion rate=32.36 g/m$^2$·h, corrosion inhibition efficiency=73.06%, corrosion inhibitor rating:—

Molar ratio of the starting materials: pentaethylenehexamine: acetophenone: formaldehyde=1:1:1

Results of corrosion evaluation: corrosion rate=57.10 g/m$^2$·h, corrosion inhibition efficiency=52.46%, corrosion inhibitor rating:—

Conclusion: Compared with the corrosion inhibitor prepared with molar ratio of pentaethylenehexamine: acetophenone: formaldehyde=1:2:2 and 1:1:1, when the molar ratio of the starting materials is the feeding ratio of example 2, that is, pentaethylenehexamine: acetophenone: formaldehyde=1:6:6, the corrosion inhibition efficiency increases by 22.87% and 43.47% respectively, and the corrosion inhibitor rating increases at least two grades for both cases.

COMPARISON EXAMPLE 3

Preparation conditions: pH=3, reaction temperature=80° C., reaction time=2 h, that is, the reaction condition of example 3.

Molar ratio of the starting materials:tetraethylenepentamine:cyclohexanone:formaldehyde=1:2:2

Results of corrosion evaluation: corrosion rate=8.68 g/m$^2$·h, corrosion inhibition efficiency=92.77%, corrosion inhibitor rating: Grade 3

Molar ratio of the starting materials:tetraethylenepentamine:cyclohexanone:formaldehyde=1:1:1

Results of corrosion evaluation: corrosion rate=21.01 g/m$^2$·h, corrosion inhibition efficiency=82.51%, corrosion inhibitor rating:—

Conclusion: Compared with the corrosion inhibitor prepared with molar ratio of tetraethylenepentamine:cyclohexanone:formaldehyde=1:2:2 and 1:1:1, when the molar ratio of the starting materials is the feeding ratio of example 3, that is, tetraethylenepentamine:cyclohexanone:formaldehyde:trioxane (equivalent formaldehyde)=1:5:2:3, the corrosion inhibition efficiency increases by 3.43% and 13.69% respectively, and the corrosion inhibitor rating increases one and two grades, respectively.

COMPARISON EXAMPLE 4

Preparation conditions: pH=5, reaction temperature=75° C., reaction time=2 h, that is, the reaction condition of example 4.

Molar ratio of the starting materials:triethylenetetramine: acetophenone:formaldehyde=1:4:4

Results of corrosion evaluation: corrosion rate=1.98 g/m$^2$·h, corrosion inhibition efficiency=98.35%, corrosion inhibitor rating: Grade 1

Molar ratio of the starting materials:triethylenetetramine: acetophenone:formaldehyde=1:2:2

Results of corrosion evaluation: corrosion rate=1.44 g/m$^2$·h, corrosion inhibition efficiency=95.48%, corrosion inhibitor rating: Grade 3

Molar ratio of the starting materials: triethylenetetramine: acetophenone:formaldehyde=1:1:1

Results of corrosion evaluation: corrosion rate=9.92 g/m²·h, corrosion inhibition efficiency=91.74%, corrosion inhibitor rating: Grade 3

Conclusion: Compared with the corrosion inhibitor prepared with molar ratio of triethylenetetramine:acetophenone:formaldehyde=1:2:2 and 1:1:1, when the molar ratio of the starting materials is the feeding ratio of example 4, that is, triethylenetetramine:acetophenone:formaldehyde=1:4:4, the corrosion inhibition efficiency increases by 2.87% and 6.61% respectively, and the corrosion inhibitor rating increases two grades for both cases.

Note: Corrosion evaluation method is petroleum and natural gas industry standards of the People's Republic of China SY/T5405-1996 "Testing method and evaluation index for properties of acidizing corrosion inhibitor", static weight loss method at atmospheric pressure is used, the corrosion system is 90° C., 15% HCl, corrosion time of 4 h, the level of Mannich base corrosion inhibitor is 1% by weight of acid solution, corrosion sheet is N80 steel sheet. The equation for calculating the corrosion rate is:

V=(weight of specimen before corrosion−weight of specimen after corrosion)/(surface area of test pieces×corrosion time)

The technical features as described above constitute the examples of the present invention, which have high adaptability and good technical effect, and if necessary, unnecessary technical features can be added or omitted according to the practical need to satisfy the requirements of different situations.

INDUSTRIAL APPLICABILITY

The advantages of the present invention using the technical solutions described above over the prior art are as follows:

Organic polyamines comprising three or more primary amine groups and/or secondary amine groups are used as the amine component in the starting materials. The three or more primary amine groups and/or secondary amine groups of the organic polyamines are caused to undergo Mannich reaction with ketone and aldehyde, respectively, thereby sufficiently utilizing the organic polyamines to perform the grafting of the functional groups on a plurality of amine groups to obtain multi-branched Mannich base corrosion inhibitor having stereo structures. Consequently, the adsorption centers of the resulting product are increased and can form multi-point adsorption with metal surface, so that compared with Mannich base corrosion inhibitor having linear structures, the adsorption film formed is better secured and has stronger adsorption force. Meanwhile, the molecular chain of Mannich base corrosion inhibitor having stereo structures is longer than that of linear Mannich base of prior art. When the metal wall surface has been corroded or is unsmooth, the Mannich base corrosion inhibitor having stereo structures exhibits bridging or multi-molecular entangled bridging, and thus shows good corrosion inhibition effect. In summary, compared with the linear Mannich bases of prior art, the Mannich base having stereo structures, or referred to as chiral Mannich base corrosion inhibitor shows strong adsorption force, high film strength, high film compactness, increase in corrosion inhibition efficiency by at least 2%, and increase in corrosion rating by at least one grade. Said Mannich base corrosion inhibitor overcomes the disadvantages in prior art of few adsorption centers, single adsorption group and weak adsorption force to metal surfaces.

What is claimed is:
1. A multi-branched Mannich base corrosion inhibitor, characterized by the structure of:

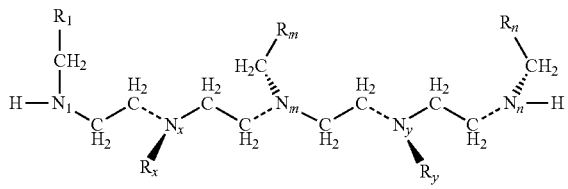

wherein
$N_1$, $N_x$, $N_y$, $N_m$, and $N_n$ are nitrogen atoms on C—N skeleton, x, y, m and n are sequence numbers thereof, and $2 \leq x \leq m \leq y \leq n-1$, and $3 \leq n \leq 7$;
$R_1$, $R_m$ and $R_n$ are substituents in starting material ketone after the substitution of active hydrogen on the carbon atom linked to carbonyl, and are aliphatic ketone group, alicyclic ketone group and aromatic ketone group, respectively; the ketone group within the ring of the alicyclic ketone groups is selected from the group consisting of cyclohexanone group, cyclopentanone group, o-methyl cyclohexanone group, p-methyl cyclohexanone group, 2-methyl cyclopentanone group, 2-ethyl cyclopentanone group, 3-ethyl cyclopentanone group, and the aliphatic ketone group, aromatic ketone group and other alicyclic ketone group are represented by the following formula:

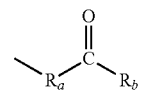

wherein $R_a$ and $R_b$ each independently represents $C_1$-$C_6$ alkyl, $C_6$-$C_9$ linear or branched aryl, $C_5$-$C_9$ linear or branched cycloalkyl group;
$R_x$ and $R_y$ are H or

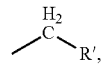

$R_x$ and $R_y$ are H or
R' is substituent in starting material ketone after the substitution of active hydrogen on the carbon atom linked to carbonyl, and is aliphatic ketone group, alicyclic ketone group and aromatic ketone group, respectively; the ketone group within the ring of the alicyclic ketone group is selected from the group consisting of cyclohexanone group, cyclopentanone group, o-methyl cyclohexanone group, p-methyl cyclohexanone group, 2-methyl cyclopentanone group, 2-ethyl cyclopentanone group, 3-ethyl cyclopentanone group, and the aliphatic ketone group, aromatic ketone group and other alicyclic ketone group are represented by the following formula:

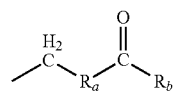

wherein $R_a$ and $R_b$ each independently represents $C_1$-$C_6$ alkyl, $C_6$-$C_9$ linear or branched aryl, $C_5$-$C_9$ linear or branched cycloalkyl group.

2. A method for preparing the multi-branched Mannich base corrosion inhibitor of claim 1, characterized by, (1) adding 3-7 moles ketone and 3-7 moles aldehyde to reaction kettle, adjusting pH to 2-6 with acid, controlling temperature to 20-50° C. and stirring for 20-30 mins;

(2) adding 1 mole organic polyamine to the reaction kettle under stirring, or adding the pH-adjusted ketone, aldehyde and organic solvent to organic polyamine, controlling temperature to 60-90° C. and reacting for 1-3 hrs, and after completion of the reaction, heating the system to 110° C. under nitrogen to remove water;

the organic polyamine is organic compound comprising three or more primary amine groups and/or secondary amine groups;

the ketone is selected from the group consisting of aliphatic ketone, alicyclic ketone, aromatic ketone and the combination thereof.

3. The method for preparing the multi-branched Mannich base corrosion inhibitor of claim 2, characterized in that the organic polyamine is selected from the group consisting of diethylenetriamine, triethylenetetramine, tetraethylenepentamine, pentaethylenehexamine, hexaethyleneheptamine or combinations thereof.

4. The method for preparing the multi-branched Mannich base corrosion inhibitor of claim 2, characterized in that the ketone group within the ring of the aliphatic ketone is selected from the group consisting of cyclohexanone, cyclopentanone, cycloheptanone, o-methyl cyclohexanone, p-methyl cyclohexanone, 2-methyl cyclopentanone, 2-ethyl cyclopentanone, and 3-ethyl cyclopentanone.

5. The method for preparing the multi-branched Mannich base corrosion inhibitor of claim 2, characterized in that the aliphatic ketone, aromatic ketone and alicyclic ketone are represented by the following formula:

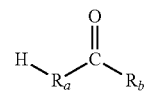

wherein $R_a$ and $R_b$ each independently represents $C_1$-$C_6$ alkyl, $C_6$-$C_9$ linear or branched aryl, $C_5$-$C_9$ linear or branched cycloalkyl group.

6. The method for preparing the multi-branched Mannich base corrosion inhibitor of claim 2, characterized in that the aldehyde is formaldehyde or polyformaldehyde capable of dissociating out formaldehyde.

7. The method for preparing the multi-branched Mannich base corrosion inhibitor of claim 2, characterized in that the organic solvent added during the reaction is one of methanol, ethanol and petroleum ether.

8. The method for preparing the multi-branched Mannich base corrosion inhibitor of claim 2, characterized in that the acid used for adjusting pH value is one of hydrochloric acid, formic acid and acetic acid.

* * * * *